United States Patent [19]

Dohring et al.

[11] 4,037,590
[45] July 26, 1977

[54] POINT PRESSURE THERAPY DEVICE

[76] Inventors: Albert A. Dohring; Grace H. Dohring, both of 24028 Union, Dearborn, Mich. 48124

[21] Appl. No.: 632,366

[22] Filed: Nov. 17, 1975

[51] Int. Cl.² ............................................. A61H 39/00
[52] U.S. Cl. ..................... 128/24.4; 128/57; 128/303.13; 128/329 A; 128/405
[58] Field of Search ........... 128/303.1, 303 R, 303.13, 128/303.14, 303.17, 303.18, 303.19, 329 A, 362, 404–409, 2.1 C, 2 R, 24.3, 24.4, 57; 73/81

[56] References Cited

U.S. PATENT DOCUMENTS

| 712,220 | 10/1902 | Vetter | 128/406 |
| 1,273,056 | 7/1918 | George | 128/409 X |
| 2,204,295 | 6/1940 | Brockman | 128/404 |
| 2,208,023 | 7/1940 | Ellis | 128/404 |
| 2,323,925 | 7/1943 | Markwardt | 73/81 |
| 2,480,029 | 8/1949 | Jozsy | 128/24.4 |
| 3,498,120 | 3/1970 | MacMillan | 73/81 |
| 3,625,202 | 12/1971 | Oyoshirhara | 128/24.3 |
| 3,923,064 | 12/1975 | Leupold | 128/329 A |
| 3,933,148 | 1/1976 | Wyler et al. | 128/2 R |

FOREIGN PATENT DOCUMENTS

| 487,265 | 11/1929 | Germany | 128/407 |
| 283,516 | 5/1950 | Switzerland | 128/24.4 |

Primary Examiner—Robert W. Michell
Assistant Examiner—Lee S. Cohen
Attorney, Agent, or Firm—Allan J. Murray

[57] ABSTRACT

A small ball of desired size, to be pressed against the skin of a human patient in an area requiring therapy, is revolubly mounted in an end portion of a carrier which protrudes from a holder, with a portion of the carrier received in the holder for reciprocable sliding travel, therein, and a spring member carried in the holder to urge the carrier in one direction of reciprocable sliding travel, with the holder preferably carried by an elongated handle; the holder, and carrier being electrically conductive, and electrical circuitry carried by the handle and electrically connected to the holder whereby mild electrical current may be employed during therapy.

6 Claims, 3 Drawing Figures

POINT PRESSURE THERAPY DEVICE

BACKGROUND OF INVENTION

This invention derives from the field of acupuncture, and is intended to afford a pressure "point" therapy for humans or animals which does not entail puncturing the skin and imbedding needles as in conventional acupuncture. In the practice of acupuncture, areas of the body which may benefit from acupuncture treatment are located and marked or otherwise indicated, and subjected to the usual treatment.

Some such areas will respond to treatment which does not necessarily involve piercing the skin. This treatment may consist of a steady pressure upon a specific area, prolonged for a desired period, or it may concist of a rhythmical, or arhythmical variation in the pressure.

When applying a rapid variation in pressure, it is desirable not to totally interrupt the contact by inadvertently removing the ball from its point of contact with the skin of a patient because the identical point of contact may not be easily recovered, and also it constitutes an interruption in the therapy. As may be clear from the following information, the instant device provides a means for gently varying the applied pressure without losing contact with the area being treated.

Earlier searches in the field of acupuncture as such, produced nothing of significance, and therefore no search has been made prior to the filing of the present application. However, applicant is unaware of any prior art which might be even remotely pertinent.

SUMMARY OF INVENTION

Invention lies in the provision of a holder adapted to slidably receive a carrier for the aforesaid ball, and of a carrier adapted to be so slidably received in the holder, and further in the provision of a spring to yieldably urge the carrier toward one end of its sliding travel, and to maintain pressure upon the carrier, and consequently the ball member, while varying said pressure in response to variation of compression of said spring, and in the provision of a handle member to carry said holder, and in electrical circuitry affording conduction of a gentle current to said ball.

This invention is attained by the device hereinafter described, and illustrated in the accompanying drawing, wherein.

Figure 1:
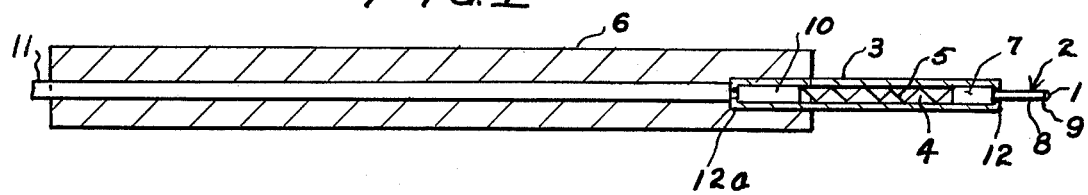
FIG. 1 is a longitudinal section on a horizontal axis of the device.
Figure 2:
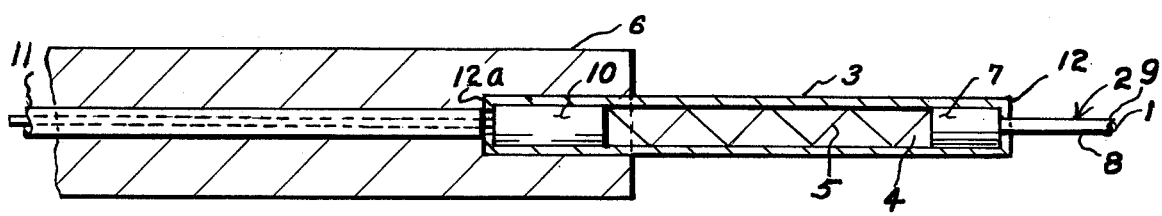
FIG. 2 is a partial sectional view similar to FIG. 1, but on a substantially larger scale.

In these views the reference character 1 indicates the ball "point" or pressure member, which is not pointed and will not puncture the human skin. Said pressure member 1 is revolubly carried by a carrier 2, as hereinafter described, and the carrier has an end portion 7 receivd in an end portion of a holder 3. The holder is formed with a hole 4 extending along its longitudinal axis. A compression spring 5 is disposed in said holder to react against the carrier 2, and urge said carrier and the pressure member 1 to the right seen in the views.

A handle 6 is apertured along its longitudinal axis to firmly receive an end portion of the holder 3, and to provide a means for handling the instrument.

Figure 3:
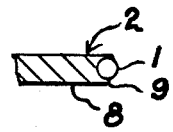
FIG. 3 is a partial sectional view on a still larger scale, illustrating the ball member as secured terminally in the carrier.

A manner of constructing the carrier is to form one end portion 7 thereof as a piston, from which there may integrally extend a rod 8. The outer end portion of the rod is radially arcuately socketed to revolubly carry the pressure member 1, which is in the form of sphere, as may most clearly seen in FIG. 3. The marginal end portion of the carrier is crimped at 9 just beyond the center of the ball to secure the ball to revolve in the socket. The spacer 10 may be disposed in the hole 4 if desired, to increase the compression of the spring 5. Further, wire 11 may extend through the handle to have electrical communication with the holder 3, and thus with the carrier 2 and the pressure member 1. It is intended, of course, that electrical current would be carefully controlled so as to avoid possibility of serious shock. The pressure member 1, carrier 2 and 7, spring 5, and spacer 10 are all of electrically conductive material.

As may now be clear, the piston 7 of the carrier 2 is intended to have reciprocable travel in the hole 4 of the holder 3. The rod 8 extends from the end of said hole, and to resist escape of the piston 7 through the open end of the hole, a marginal end portion 12 of the holder is bent radially inwardly. The opposite end portion 12a is similarly bent.

Having located an area on a human or animal body that may benefit from this particular form of therapy, the pressure member 1 is placed on the indicated area, and an operator or physician holding the device by the handle, which handle is of electrically non-conductive material, may reciprocate the handle and holder toward and from the area being treated. The spring 5 engaging an end face of the piston 7 will yield as the handle is forced toward such area, and this will serve to intensify the pressure applied to the area. Obviously, as the handle moves from the area being trearted, the spring 5 will expand, reducing the pressure applied to the area.

Thus an area which may respond to this particular form of treatment may receive such treatment without interruption by loss of contact of the pressure point, which might occur in the absence of the spring.

Were the device made without a revolubly mounted ball; if the skin-contacting end were not spherical, and not revoluble, the instrument would drag across the skin of a patient, rather than roll. Thus, such instrument could itself cause pain and discomfort by friction, or by catching the skin as it passes over such skin. This, in itself, can cause a reaction to a "false sympton" induced by the instrument itself, and could result in treating areas that will not respond to treatment.

A further advantage is that the ball makes a small temporary indentation in the skin. Since adhesive patches of material are available with a ball carried by each patch, such a device can be applied, with the ball fitted into said indentation to maintain a gentle pressure on the treated area when deemed desirable.

What we claim is:

1. A therpeutic device to apply localized pressure, including, a pressure member, an elongated carrier for said pressure member, a carrier holder elongated on longitudinal axis, a hole formed in said holder elongated on and approximately concentric with said longitudinal axis, said carrier including a piston, said piston being received in said hole to support said carrier for reciprocable sliding travel along said longitudinal axis, said piston having an inner end face, means to resist escape of said piston from said hole, said carrier further including a rod portion slidably protruding through said means to resist escape, said rod portion being a smaller diameter than said piston, said rod portion revolubly and terminally carrying said pressure member exteriorly of said holder for application to the skin of a patient, means carried by said holder effective upon said piston to urge said carrier under variable pressure toward the skin of patient in the use of the device.

2. In a device as set forth in claim 1, said means to urge being a yieldably resistant means housed in said holder to react between said holder and the inner end face of said piston, to afford reciprocable manipulation of the device and variation of said pressure.

3. In a device as set forth in claim 2, said yieldably resistant means being compression spring reacting between said holder and said piston to urge said carrier outwardly of said holder.

4. A device as set forth in claim 3, further including a handle, said holder being secured in said handle, whereby the device may be applied by manually gripping said handle.

5. In a device as set forth in claim 4, said holder having an inner end portion embedded in said handle, and a terminal outer portion, said means to resist escape being said terminal outer portion of said holder, said terminal outer portion being deformed to resist escape of said piston from said holder.

6. In a device as set forth in claim 5, said handle being of electrically non-conductive material, electrically conductive means carried by said handle for making an electrical connection to a source of current, and electrically communicating with said holder, said holder, said compression spring, said carrier, and said pressure member being of electrically conductive material, and electrically communicating in series, whereby a desired electrical current from a source of said current may be conducted to the skin of a patient receiving therapy.

* * * * *